(12) United States Patent
Perry

(10) Patent No.: US 11,504,457 B2
(45) Date of Patent: Nov. 22, 2022

(54) WOUND IRRIGATION SYSTEM

(71) Applicant: Travis L. Perry, Dayton, OH (US)

(72) Inventor: Travis L. Perry, Dayton, OH (US)

(73) Assignee: Travis L. Perry, Dayton, OH (US)

( * ) Notice: Subject to any disclaimer, the term of this patent is extended or adjusted under 35 U.S.C. 154(b) by 59 days.

(21) Appl. No.: 17/082,703

(22) Filed: Oct. 28, 2020

(65) Prior Publication Data

US 2021/0228786 A1 Jul. 29, 2021

Related U.S. Application Data

(60) Provisional application No. 63/006,945, filed on Apr. 8, 2020, provisional application No. 62/967,367, filed on Jan. 29, 2020.

(51) Int. Cl.
*A61M 1/00* (2006.01)
*A61M 39/08* (2006.01)
(Continued)

(52) U.S. Cl.
CPC ..... *A61M 1/0058* (2013.01); *A61F 13/00068* (2013.01); *A61M 1/90* (2021.05);
(Continued)

(58) Field of Classification Search
CPC ........ A61M 1/0058; A61M 1/90; A61M 1/76; A61M 39/22; A61M 27/00; A61F 13/00068; A61F 13/0216; A61F 13/00
See application file for complete search history.

(56) References Cited

U.S. PATENT DOCUMENTS

| 8,974,428 B2 | 3/2015 | Freedman et al. |
| 10,300,182 B1 | 5/2019 | Brar |

(Continued)

FOREIGN PATENT DOCUMENTS

| CN | 201510631 U | 6/2010 |
| CN | 201668852 U | 12/2010 |

(Continued)

OTHER PUBLICATIONS

International Search Report and Written Opinion dated May 18, 2021 pertaining to International PCT Application No. PCT/US2021/015605 filed Jan. 29, 2021.

D. Alan Aubrey, et al.; "Treatment Of The Perineal Wound After Proctectomy By Intermittent Irrigation"; Arch. Surg.; Oct. 1, 1984; pp. 1141-1144.

(Continued)

*Primary Examiner* — Adam Marcetich
*Assistant Examiner* — Meagan Ngo
(74) *Attorney, Agent, or Firm* — Dinsmore & Shohl LLP

(57) ABSTRACT

A wound irrigation system and method of making and using. The system uses a pored, closed-ended delivery conduit to enhance the consistency and speed with which anti-microbial or related irrigation fluids may be delivered in order to promote cleansing, debridement and biofilm reduction in wounds. The ease of use of the system as a moist wound healing cascade makes it applicable to both in-home and in-facility environments that is not offered through traditional instillation negative pressure systems. In one form, the fluid delivery conduit is used as part of a dual-conduit approach in order to also help promote the removal of drainage, waste, irrigation overflow or other fluid from the wound. Utilization of such a pored, closed-ended delivery conduit in conjunction with a separate drainage conduit infusing helps reduce the frequency of dressing changes as well as the likelihood of microorganism formation and colonization.

18 Claims, 11 Drawing Sheets

(51) Int. Cl.
*A61F 13/00* (2006.01)
*A61M 39/20* (2006.01)

(52) U.S. Cl.
CPC ............ *A61M 39/08* (2013.01); *A61M 39/20* (2013.01); *A61M 2205/3324* (2013.01); *A61M 2205/3327* (2013.01); *A61M 2205/50* (2013.01)

(56) References Cited

U.S. PATENT DOCUMENTS

| | | | | |
|---|---|---|---|---|
| 2002/0150720 | A1* | 10/2002 | Howard | B32B 27/08 428/131 |
| 2009/0204084 | A1* | 8/2009 | Blott | A61M 27/00 604/290 |
| 2010/0168654 | A1* | 7/2010 | Tout | A61M 1/743 604/31 |
| 2011/0054283 | A1 | 3/2011 | Shuler | |
| 2012/0123323 | A1 | 5/2012 | Kagan et al. | |
| 2014/0066868 | A1* | 3/2014 | Freedman | A61M 3/0283 604/319 |
| 2016/0015872 | A1 | 1/2016 | Luckemeyer et al. | |
| 2017/0209641 | A1* | 7/2017 | Mercer | A61M 1/85 |
| 2018/0064841 | A1* | 3/2018 | Stoecker | A61F 13/0216 |
| 2018/0214315 | A1* | 8/2018 | Mercer | A61F 13/00987 |
| 2018/0256405 | A1* | 9/2018 | Yen | A61M 27/00 |
| 2020/0237977 | A1* | 7/2020 | Panotopoulos | A61B 5/031 |
| 2021/0060217 | A1* | 3/2021 | Locke | A61F 13/00068 |
| 2021/0205527 | A1* | 7/2021 | Pratt | A61F 13/0216 |

FOREIGN PATENT DOCUMENTS

| | | |
|---|---|---|
| CN | 202113477 U | 1/2012 |
| CN | 207400851 U | 5/2018 |
| CN | 109621024 A | 4/2019 |
| CN | 109731151 A | 5/2019 |
| CN | 209108211 U | 7/2019 |
| CN | 209253768 U | 8/2019 |
| GB | 2431351 A | 4/2007 |
| WO | 2014184674 A2 | 11/2014 |
| WO | 2017215418 A1 | 12/2017 |
| WO | 2018210692 A1 | 11/2018 |

OTHER PUBLICATIONS

Tom Wolvos; "Wound Instillation The Next Step In Negative Pressure Wound Therapy. Lessons Learned From Initial Experiences"; Wound Management and Prevention; vol. 50; Issue 11; Nov. 2004.

Kiyokawa Kensuke, et al.; "New Continuous Negative-Pressure and Irrigation Treatment for Infected Wounds and Intractable Ulcers"; Plastic and Reconstructive Surgery Journal of the American Society of Plastic Surgeons; Mar. 24, 2006.

Su-Shin Lee, et al.; "Does Continuous Negative-Pressure And Irrigation Treatment Really Rinse The Whole Closed Wound?"; Plastic and Reconstructive Surgery; vol. 122; No. 1; Jul. 2008; pp. 319-320.

H. Teder, et al; Continuous Wound Irrigation In The Pig; Journal Investigative Surgery; Jul. 9, 2009; pp. 399-407.

En-Xu Bi, et al.; "Clinical Research Of Self-Prepared Negative Pressure Dual-Tubes Combined With Chinese Medical Irrigation And Drainage In Treatment Of High Perianal Abscess"; Jan. 1, 2010.

Keigo Morinaga, et al.; "Results Of Intra-Wound Continuous Negative Pressure Irrigation Treatment For Mediastinitis"; Journal of Plastic Surgery and Hand Surgery; vol. 47; May 28, 2013.

* cited by examiner

WOUND IRRIGATION SYSTEM

This application claims the benefit of U.S. Provisional Application Ser. No. 62/967,367 filed Jan. 29, 2020 and U.S. Provisional Application Ser. No. 63/006,945 filed Apr. 8, 2020.

The present specification generally relates to a wound irrigation system (WIS) and method for wound healing, and more specifically to a WIS that achieves improved wound moisture maintenance, healing and bioburden reduction through increased control of the delivery of irrigation fluid to—and optionally and the removal of wound drainage fluid from—a wound site.

BACKGROUND

There is ample evidence that illustrates that optimal wound healing requires a moist physiological environment for cells to function properly. Wound anti-microbial irrigations—when routinely administered perioperatively—have shown to be associated with higher first-time closure success, reduced debridement and number of procedures, as well as reduction of chronic inflammation from bacterial overgrowth.

Often, due to variability in techniques, procedures, training and staffing, the benefits associated with uniform moist wound care are forfeited. This can lead to diminished physiological properties of wound healing, including reduced angiogenesis and granulation tissue formation, as well as traumatic dressing changes and desiccated wound beds that cause pain and anguish for patients.

In one conventional approach (known as wet-to-dry dressing), a wound (or wound bed) is filled with moist, damp packing (or gauze) and subsequently covered. Over the course of wound healing, the initially moist gauze starts to dry out. On its own, such an approach lacks consistent moisture maintenance of the wound environment due at least in part to variations in wound care techniques and evaporative loss from a wound. As such, this approach requires more frequent removal of gauze dressings to rewet and reapply an anti-microbial solution in order to keep the dressing from drying out. This tendency of the dressing to dry out and the concomitant need to replenish moisture in turn increases mechanical disruption of healthy wound bed granulation and epithelial cells. Increase pain is also associated with frequent changes due to dry dressing and wound desiccation. In addition, the amount of physician or other caregiver oversight required is such that this approach is often performed only on an inpatient basis, which in turn increases the time, cost and patient inconvenience associated with wound care.

Another approach, known as negative pressure wound therapy (NPWT), has shown promise through the controlled application of sub-atmospheric pressure to the wound. In NPWT, a piece of sterile tubing is used as a part of a wound closure system to create a generally airtight connection between a pump or related vacuum source and a sealed dressing at the wound site. Such tubing acts as a conduit to help remove excess irrigation fluid, as well as waste materials (such as wound exudate, infectious materials or the like) from the wound to a separate container. Nevertheless, the NPWT irrigation systems are more efficacious in large wound volumes, as well as in those wounds requiring longer instillation and indwelling times. As such, it has proved difficult to employ traditional NPWT approaches in smaller and more complex wounds, as the risk of seal disruption to the NPWT dressing is increased. Furthermore, the tubing used as part of conventional NPWT approaches are integrated into the vacuum source, making it more difficult, bulky and less versatile to use in outpatient situations, particularly when dressing changes may need to take place with a relatively high frequency, or where the person changing the dressing does not have a lot of wound-specific medical training.

Accordingly, a need exists for a wound irrigation, debridement, cleansing and moisture maintenance system for efficient and cost-effective wound care. A need further exists for utilizing traditional wet-to-dry and NPWT dressing changes in a manner that makes them applicable to a larger class of wound types and sizes. A need still further exists for a wound irrigation, debridement, cleansing and moisture maintenance system that is versatile and could be utilized on an outpatient or inpatient basis.

SUMMARY

According to an aspect of the present disclosure, a WIS is disclosed. The WIS includes tubing in the form of a delivery conduit for the conveyance of one or more fluids to a wound bed. The delivery conduit has a proximal end and a distal end that are fluidly separated from one another by a medial portion to define a fluid flow path. The medial portion additionally has numerous apertures extending along its length and through its wall. In this way, a majority of the fluid that is introduced within the delivery conduit at its proximal end is placed in fluid communication with the wound bed through the medial portion. In one optional form, the WIS may additionally include a drainage conduit configured such that upon its placement adjacent or within the wound bed, it may be used to convey at least a portion of any excess moisture present within the wound bed. In such optional form, the inclusion of a separate removal or drainage conduit allows the delivery conduit to avoid having to perform both fluid delivery and removal duties and instead be used exclusively for fluid delivery such that cross-contamination issues associated with the conveyance of both irrigation and excess or waste fluids is minimized or eliminated.

According to another aspect of the present disclosure, a moisture, humidification and pH monitoring device is disclosed. Such a system includes at least the tubing in the form of a delivery conduit as previously described in the previous aspect.

According to another aspect of the present disclosure, a wound irrigation treatment system is disclosed. Such a system includes at least the tubing in the form of a delivery conduit as previously described in the previous aspects.

According to another aspect of the present disclosure, a method of using a WIS is disclosed. Such a method includes at least the tubing in the form of a delivery conduit as previously described in the previous aspects.

According to another aspect of the present disclosure, a wound irrigation retrofit kit is disclosed. The wound irrigation retrofit kit includes the WIS of the previous aspect, as well as additional components that are discussed in more detail as follows.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

In the present disclosure, a wound (or wound site or wound bed) may be treated with a WIS or assembly that includes the WIS. In one form, the wound is a chronic wound, higher-degree burn or the like, although it will be appreciated that the precise nature of such wound is not critical to the applicability of the WIS. In one form, the WIS may be used for various forms of wound treatment such as one or more of cleansing, debridement, moisturizing and bioburden reduction. Such an approach promotes the more rapid formation of new cell growth without the complexity of repeated gauze or dressing changes.

Figure 1A:
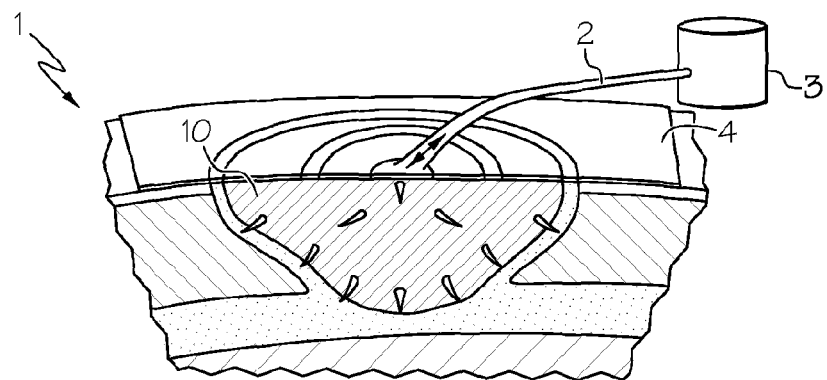
FIG. 1A depicts a wound that is being treated by a vacuum-based system according to the prior art.
Figure 1B:
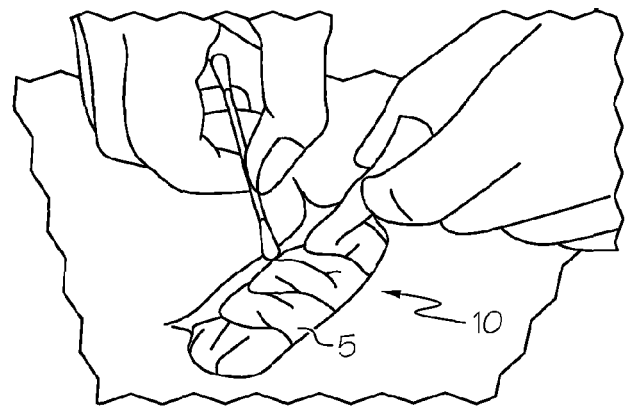
FIGS. 1B and 1C depict a wound that is being treated by a wet-to-dry gauze-based system according to the prior art.
Figure 1C:
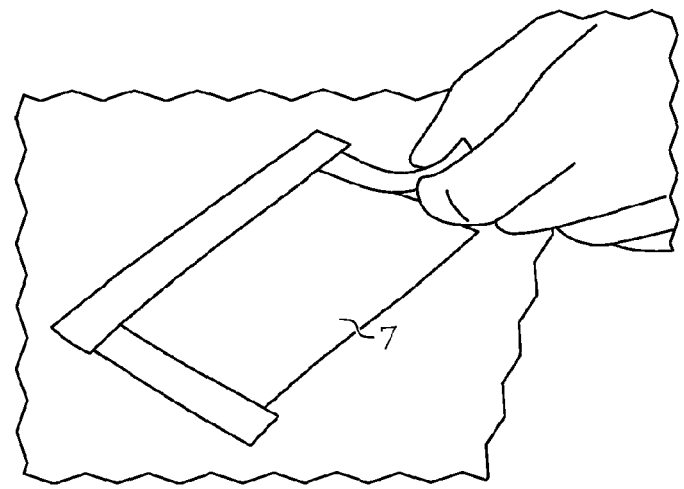

Referring first to FIGS. 1A through 1C, two different conventional approaches to treating a wound 10 according to the prior art are shown. Referring first to FIG. 1A, an NPWT 1 includes a single piece of tubing 2 that fluidly couples a vacuum source 3 to the wound 10 that is covered by a fluid-impermeable membrane 4. The tubing 2 is used both for the delivery of an irrigation fluid and the removal of excess fluid in the form of waste such that—among other things—the vacuum source 3 functions as a fluid removal source. Referring next to FIGS. 1B and 1C, both a wound-packing step (FIG. 1B) and a wound-covering step (FIG. 1C) are shown for use with a gauze-based wet-to-dry packing 5. In the wound-packing step, a moistened piece of gauze or packing is inserted into the cavity of the wound 10, while in the wound-covering step the damp packing 5 is covered with another piece of gauze or related dressing 7.

Figure 2:
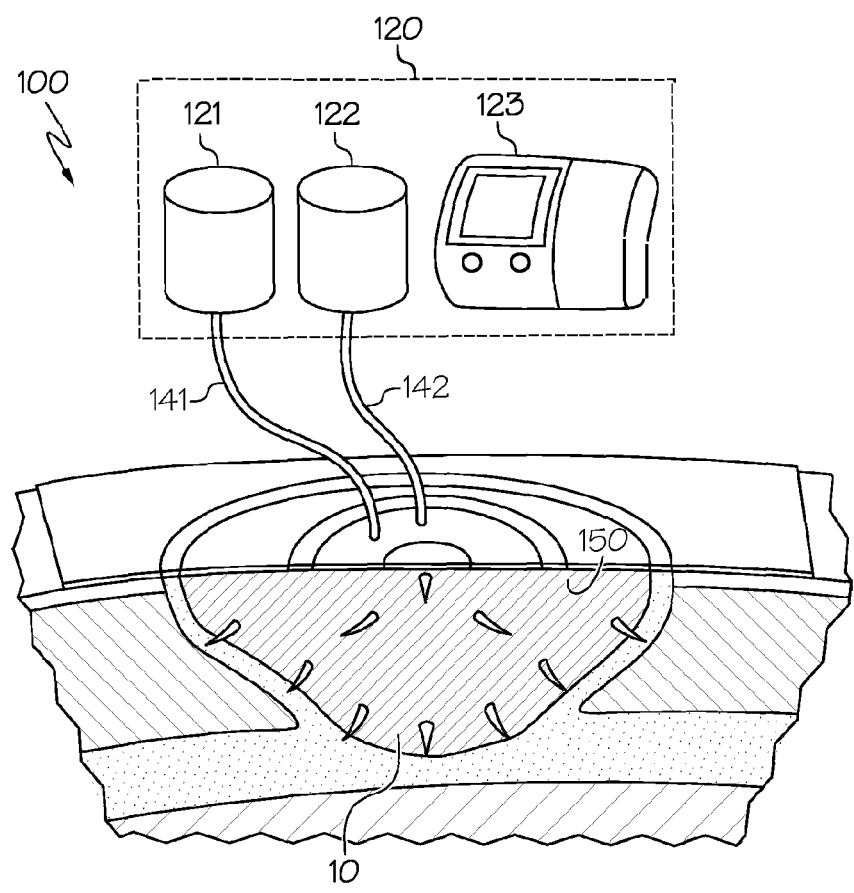
FIG. 2 depicts a wound that is being treated by a vacuum-based WIS according to an aspect of the present disclosure.

Referring next to FIG. 2, an NPWT-based embodiment of the WIS 100 according to an aspect of the present disclosure is shown for use in the treatment of a wound bed 10. The NPWT-based embodiment of the WIS 100 includes an NPWT device 120 that in one form is made up of an irrigation fluid delivery source 121 and an excess fluid removal source 122, along with a user-operable control panel 123. In one form, the irrigation fluid delivery source 121 is in the form of a pump, such as one receiving pneumatic, hydraulic or electric power. The excess removal source 122 (which in form may include a vacuum) relies upon a low pressure for the suction-based removal of excess moisture that may include one or more of waste, drainage or related exudate. In one form, the low pressure needed for operation of the excess fluid removal source 122 may be provided by a pump, where in one form it can be the same pump as that used to provide the pressure to the irrigation fluid delivery source 121, and in another form an entirely separate pump. Although presently shown as being two separate pieces of equipment that may be contained within two separate housings, it will be appreciated that the irrigation fluid delivery source 121 and excess fluid removal source 122 may also be embodied as one or both of a single piece of equipment or contained with a single housing, and that all such variations are within the scope of the present disclosure. A dressing (such as a wound seal) 130 may also be included. In one form, the dressing 130 is a piece of relatively non-permeable membrane or the like that is capable of providing a vacuum-based barrier between the wound bed 10 and sponge 150 underneath and the ambient environment in a manner similar to well-known plastic wrap that is used to cover a refrigerated food dish. In this manner, the dressing 130 is cooperative with the NPWT device 120 such that together they permit the wound bed 10 to exist relatively free of the ambient environment.

Conduit in the form of medical tubing (or more simply, tubing) 140 allows fluids (such as an anti-microbial irrigation fluid) to be delivered to the wound bed 10 in a manner discussed in more detail as follows. In one form, such tubing 140 may include intravenous (IV) tubing, catheter tubing or the like, and that all such tubing used for wound treatment used on humans or animals are deemed to be within the scope of the present disclosure. In addition, the sponge 150 or related porous packing may optionally be used in order to provide or otherwise form a catheter-like predetermined delivery path for the fluid that is being introduced through tubing 140. When formed as a single-tube device, the tubing 140 acts as a delivery conduit (also referred to herein as irrigation conduit, irrigation tubing or the like) 141. Within the present context, the medical tubing 140 is notionally depicted as having an axisymmetric-shaped cross-section. Although not shown, the medical tubing 140 may also be shaped as an ellipse, rectangle, triangle, rhomboidal, split-circle, slit or hexagon, and that these and other variants of such cross-sectional shapes are deemed to be within the scope of the present disclosure.

In one optional form, the tubing 140 may also include a drainage (or removal) conduit 142 such that it and the delivery conduit 141 each to provide dedicated fluid coupling to a respective one of the irrigation fluid delivery source 121 and excess fluid removal source 122. In this way, movement of the fluid being delivered may take place at least partially independent of a fluid (such as drainage or related waste or overflow) that is being removed. In such form, this avoids the necessity of having a single piece of conduit that must perform both delivery and removal functions, which in turn allows for—in addition to the previously-mentioned reduction in cross-contamination of delivery and removal fluids—increased precision, as well as speed with which wound bed 10 cleansing, debridement, moisturizing or related procedures may take place. In one form, the medical tubing 140 that forms the basis of the WIS 100 may form a standalone structure, while in another, it may form part of an assembly that may be used, for instance, as part of a retrofit kit for an NPWT or related system. Within the present disclosure, the various terms such as "medical tubing", "conduit" and their variants will be understood to refer to the delivery conduit 141 alone, drainage conduit 142 alone, the delivery conduit 141 and the drainage conduit 142 together, as well as either when used in conjunction with one or more of the other components discussed herein, and that any distinctions will be apparent from the context, including for those particulars where emphasis on such distinctions may be needed.

The WIS 100 also allows for anti-microbial instillation of complex necrotizing soft tissue infection wounds utilizing skin and soft tissue sparing techniques. The WIS 100 in turn affords even and diffuse instillation into NPWT or gauze dressing that lies beneath spared skin and soft tissue without requiring the wound bed 10 to be open with an even surface. As such, the WIS 100 is capable of distributing instillation directly to complex wound surfaces that are uneven, tunneled, recessed, tracking or undermined to ensure that every aspect of the wound's surface area are treated. In one form, the various pieces of tubing (discussed in more detail as follows) are structurally decoupled from one another, while in another form, they may be structurally coupled, such as through concentric placemen, side-by-side construction or the like.

Referring next to FIGS. 3A through 5, details associated with the delivery conduit 141 of the medical tubing 140 are further described. In particular, the delivery conduit 141 (as well as the drainage conduit 142 of FIG. 2) may be commonly made from known materials (such as polyvinyl chloride (PVC), polyethylene, polyurethane, rubber alternatives such as medical-grade silicone or the like). In one form, the material selection of the medical tubing 140 may be adjusted to meet a particular end-use application, as well as to meet certain structural, cost or related needs. Likewise, in one form, the medical tubing 140 may be color-coded or equipped with labels or other indicia, such as to distinguish the delivery conduit 141 and the drainage conduit 142.

Figure 3A:
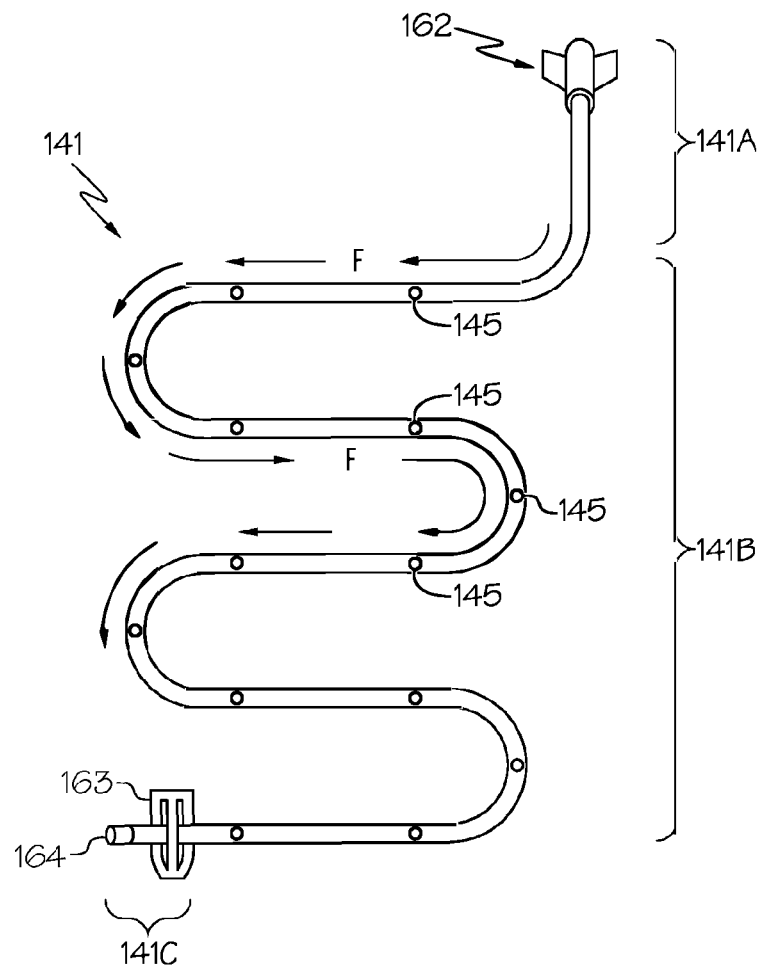
FIGS. 3A through 3D depict a section of tubing along with optional fittings and intraluminal valves according to an embodiment of the present disclosure that may be used in conjunction with either a gauze-based or NPWT-based wound treatment protocol.

Referring with particularity to FIG. 3A, the delivery conduit 141 differs from that of drainage conduit 142 in that it includes a series of axially-spaced apertures 145 each of which extend radially outward from the wall inner surface to the wall outer surface and along the length of the medial portion 141B. The delivery conduit 141 defines a proximal end 141A for the receipt of irrigation fluid, a medial portion 141B and a distal end 141C. As shown, upon the introduction of an irrigation fluid into the proximal end 141A, such fluid is made to flow (such as by gravity, pressurization or other known means) through the medial portion 141B and onto the distal end 141C along a flowpath F. In one form, the size and number of apertures (also referred to as pores) 145 is such that a majority of the irrigation fluid that is introduced into the proximal end 141A is meant to exit through the medial position 141B rather than the distal end 141C. As will be discussed in more detail as follows, this gives the WIS 100 additional flexibility in its placement within a wound bed 10 to maximize the likelihood that the irrigation fluid is being delivered to precise parts of the wound bed 10 that are in need of irrigation rather than to indiscriminately place such fluid at a remote location according to the placement of the distal end 141C. It will be appreciated that the precise length of the medial portion 141B relative to the proximal end 141A and the distal end 141C may be varied. In a like manner, the axial spacing of the apertures 145 along the flowpath F may varied at the time of tubing manufacture, thereby allowing case-specific irrigation fluid delivery capability. In this way, the spacing of the corresponding apertures 145 may be made to stop as close to or as far away from the respective conduit ends as is needed for a particular wound bed 10. In one form, the periodically-spaced apertures 145 along the medial portion 141B of the delivery conduit 141 form a drip irrigation system.

In one form, instillation of saline or related irrigation fluid may be achieved through intermittent means, such as through a pump or syringe (neither of which are shown, but could be, for example, in 10 cc, 20 cc or 60 cc increments). Depending on whether the irrigation fluid that is being introduced to the wound bed 10 is or is not being separately pressurized, the apertures 145 allow for the dripping, spraying or seepage of solutions and related fluids into one or more wound beds 110 regardless of whether such site is being treated with an NPWT-based approach as shown in FIG. 2 or an augmented wet-to-dry-based approach. The apertures 145 afford solution emission along a designated distribution of a wound bed 10, which in turn promotes the soaking of a dressing 130 (such as that depicted in FIG. 2) with an anti-microbial solution of choice. This in turn promotes efficient distribution of solutions such as this that specifically target areas of concern within a bed of the wound bed 10. Such close proximity of the point of discharge of the anti-microbial or other irrigation fluid to the location in the wound bed 10 that is in need of such fluid is further beneficial in that it reduces or eliminates fluid dwell time. Such a reduction (or even elimination) of the dwell time needed for the irrigation fluid to reach the surface of the wound bed 10 thus avoids having the conventional approaches of having the fluid travel through a substantial or even full thickness of the sponge 150, packing 105 or gauze 107 or other dressing used in the wound bed 10. Significantly, this "close proximity" placement of the tubing 140 of the WIS 100 may be used to minimize instillation volumes required to coat the surface of the wound bed 10 regardless of whether the wound being treated is small or large, simple or complex.

Figure 4:
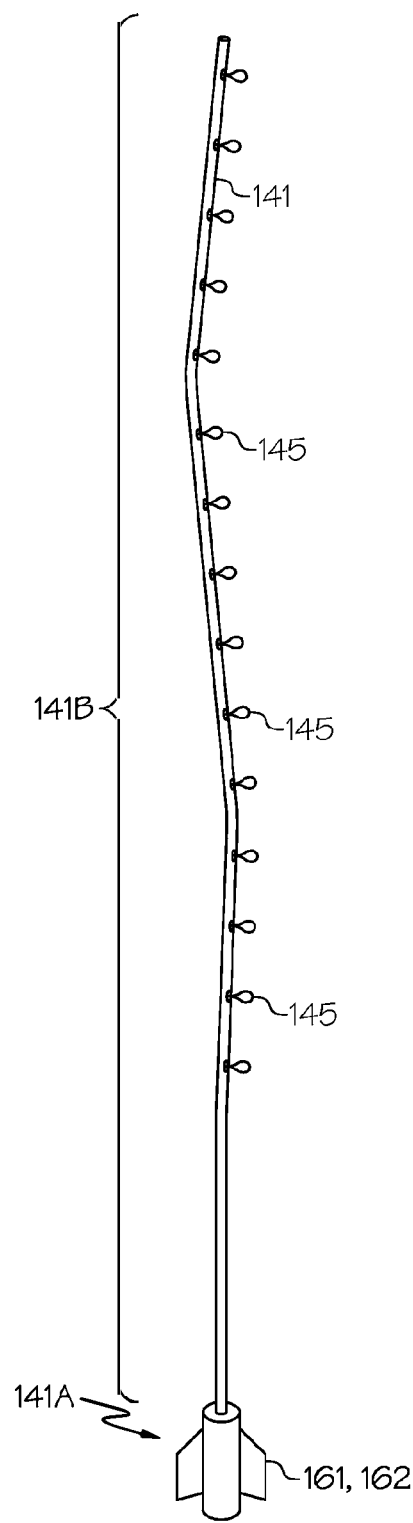
FIG. 4 depicts a section of tubing in operation where beads of water droplets form at each of the apertures that are defined along the length of the tubing.

Referring with particularity to FIG. 4, in one form, the spacing of the apertures 145 may be such that their formation occurs in regularly-spaced intervals. In addition, if provided over lengthy portions of the delivery conduit 141, there may be periodic discontinuities in the apertures 145 to allow a doctor, nurse, technician or other caregiver to cut off as much of the delivery conduit 141 as needed in order to form a delivery conduit 141 of a preferred length. In one form, the medical tubing 140 may be provided in a prepackaged form such that variations in length, pore 145 pattern, aperture 145 placement relative to the beginning and end of each preformed section of tubing 140 or other such use-specific sizes and shapes of such medical tubing 140 are readily-available to medical personnel without having to cut, splice or otherwise adjust the tubing in order to achieve a certain length or pattern distribution. This in turn may help customize the length of the delivery conduit 141 to a particular application, particularly where inventory control and ease and speed of access to a given size from among a of large quantity of such prepackaged tubing 140 is maintained, such as a hospital, trauma center or related health care facility. An example of such application of the medical tubing 140 may be the use of posterior surface tubing and anterior surface tubing where the length requirements of one differs from the other. In one form, such individual prepackaged medical tubing 140 may be provided as a set of both the delivery conduit 141 and the drainage conduit 142 (the latter, as previously mentioned, without the apertures 145) or just the delivery conduit 141 alone. As can be seen, upon pressurization of the fluid passing through the delivery conduit 141 due to the generation of various hydrostatic pressures, jets or pulses of the fluid can be seen emanating from the apertures 145 commensurate with the fluid pressure, as well as the size and shape of each aperture 145. Although FIG. 4 presently shows an irrigation fluid dripping or seeping out of some of the apertures 145, it will be appreciated that upon the application of a larger amount of pressure (such as from the pump or related irrigation fluid delivery source 121), this fluid could be expelled more as a stream, jet or other higher throughput.

Figure 3B:
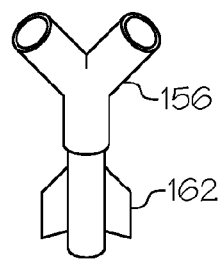

Referring again to FIG. 3A in conjunction with FIG. 3B, the medical tubing 140 in general and the delivery conduit 141 and drainage conduit 142 may employ common fitting components 160 made up of one or more connectors or other means of attachment (all shown generally as connector 161) to provide a leak free fluid coupling between it and a companion leur fitting or lock 162 for attachment to a medical instrument such as a hypodermic syringe tip (not shown). Significantly, tubing clips 163 and caps (also referred to herein as plugs) 164 allow the delivery conduit 141 to form a closure to the distal end 141C in order to promote the discharge of an irrigation fluid most—and in some cases, substantially entirely—through the axially-spaced apertures 145 that are present in the medial portion 141B. Likewise, some of the tubing clips 163 may be placed in user-defined locations along the length of the delivery conduit 141 in order to truncate the effect length of the medial portion 141B for situations where distribution of irrigating fluids over a substantial entirety of the length of the delivery conduit 141 is not desired. As shown, the permanent end closings formed by the caps 164, as well as the user-definable closured formed by the tubing clips 163, further ensure that adequate hydrostatic pressure builds up within the delivery conduit 141. In a like manner (not shown) these and other connectors 161 may be used in conjunction with the drainage conduit 142, as needed. As will be discussed in more detail as follows with regard to the delivery conduit 141, this additional pressure may be used to emit fluids out of the apertures 145 in a prescribed manner along the length.

Figures 3C, 3D:
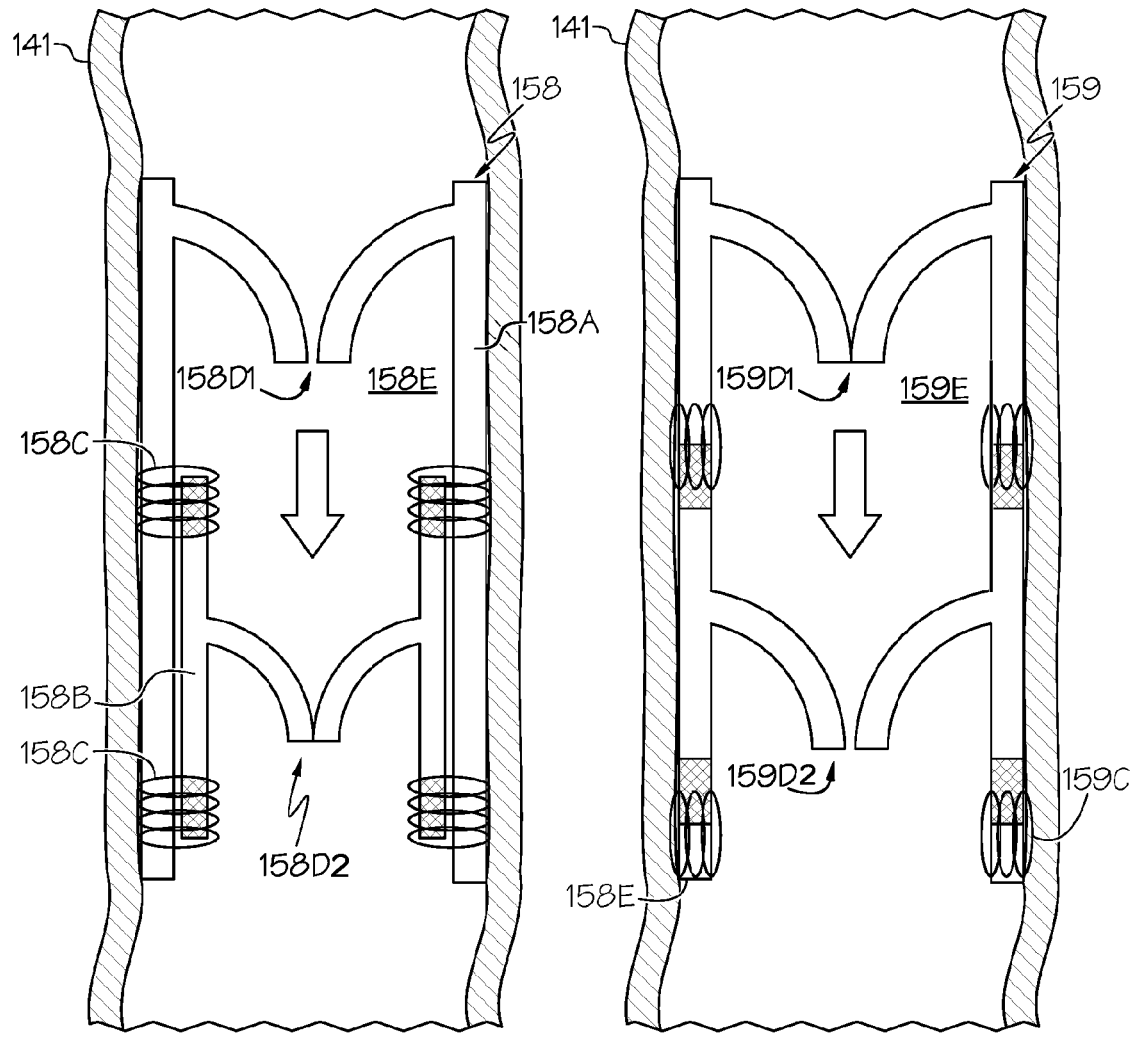

Referring with particularity to FIGS. 3C and 3D, the delivery conduit 141 may also contain one or more intraluminal valves 158 (FIG. 3C), 159 (FIG. 3D) to ensure consistent and adequate hydrostatic pressures of the irrigation fluid that is being delivered to the wound bed 10 through WIS 100. In one form, the valves 158, 159 may be formed to have a flap-like internal structure that is responsive to certain pressure fluctuations. In such a configuration, upon exceeding a certain pressure threshold with an introduced fluid, the normally-closed flaps separate to define an orifice through which the fluid may pass first into an interstitial chamber and then on to a downstream location within the delivery conduit 141. In one form, the stiffness or related mechanical properties of the material making up the flaps may be tailored in order to respond to a predetermined pressure threshold. In this way, the more downstream of the flaps may be made to open up at a different fluid pressure than that of the more upstream of the flaps. Similarly, a set of biased springs may be used in order to allow the volume defined by the interstitial chamber to expand or contract concomitant with a rise or fall in the fluid pressure within. Regardless of their precise construction, the valves 158, 159 depicted in the figures may also function in a manner similar to check valves in order to limit (or eliminate entirely) counterflow back into an upstream end of the delivery conduit 141.

Referring with particularity to FIGS. 3C and 3D, the delivery conduit 141 may also contain one or more intraluminal valves 158 (FIG. 3C), 159 (FIG. 3D) to ensure consistent and adequate hydrostatic pressures of the irrigation fluid that is being delivered to the wound bed 10 through WIS 100. In one form, the valves 158, 159 may be formed to have a flap-like internal structure that is responsive to certain pressure fluctuations. In such a configuration, upon exceeding a certain pressure threshold with an introduced fluid, the normally-closed flaps separate to define an orifice through which the fluid may pass first from an upstream location within the delivery conduit 141 into an interstitial chamber and then on to a downstream location within the delivery conduit 141. In this way, and as clearly illustrated in FIGS. 3C and 3D, the flaps of the one or more intraluminal valves 158 and 159 may be an upstream valve 158D1, 159D1 and a downstream valve 158D2, 159D2. In this manner, and as clearly illustrated in FIGS. 3C and 3D, the opening of the upstream and downstream valves 158D1, 159D1, 158D2, and 159D2 may define the orifice through which the irrigation fluid may pass through the upstream valve, the interstitial chamber 158E, 159E, and the downstream valve, to a downstream location within the delivery conduit 141. In one form, the stiffness or related mechanical properties of the material making up the flaps may be tailored in order to respond to a predetermined pressure threshold. In this way, the more downstream of the flaps may be made to open up at a different fluid pressure than that of the more upstream of the flaps. Similarly, a set of biased springs may be used in order to allow the volume defined by the interstitial chamber to expand or contract concomitant with a rise or fall in the fluid pressure within. Regardless of their precise construction, the valves 158, 159 depicted in the figures may also function in a manner similar to check valves in order to limit (or eliminate entirely) counterflow back into an upstream end of the delivery conduit 141.

Referring with even more particularity to FIG. 3D, intraluminal valve 159 may be configured to have a portion that is carrying the axially downstream one of the flaps 159D slidably movable relative to a main housing wall (which in one form may be of hollow, tubular construction), where the general movement and cooperation of the various mesh rings 159C allow for the selective movement of the downstream flap 159D. In another form (not shown), the mesh rings 158C, 159C may not be needed, instead relying solely upon the customized stiffness of the flaps 158D, 159D as a way to achieve the selective receipt into and delivery from the respective interstitial chamber 158E, 159E. In either configuration, the valves 158, 159 help to achieve (to use an electrical circuit analogy) a capacitor-like regulation of the fluid pressure.

In the embodiment shown, the fluid coupling of the valves 158, 159 and the delivery conduit 141 is achieved by the former being disposed within the latter. In another form (not shown), the construction of the valves 158, 159 may be such that they need not define a structure that fits within an inner wall of the delivery conduit 141, but instead form on an outer wall of such conduit 141 (much like a hose clamp, coupling or the like) to be placed at an end of the delivery conduit 141. Similarly (also not shown), the outer diameter of the housing of the valves 158, 159 may be approximately the same as that of the delivery conduit 141, also to be secured to an end of the delivery conduit 141. It will be appreciated that any of these manners of placing the valves 158, 159 into fluid cooperation with the delivery conduit 141 are within the scope of the present disclosure.

In addition, the connectors 161, leurs 162, clips 163 and caps 164, as well as catheter tubing and other parts that make up the wound irrigation retrofit kit or related irrigation WIS assembly may define various properties that vary in tensile strength, size, geometrical shape and even be colored coding or labels. It will be appreciated that in one form, the drainage conduit 142 is made of solid-walled tubing (due to its need to at least selectively maintain a vacuum). Within the present disclosure, the wound irrigation retrofit kit includes the WIS 100 of the previous aspect, as well as these and additional components (such as gauze for a wet-to-dry wound irrigation approach, or a sponge and NPWT with fluid delivery source and vacuum source).

Referring with particularity to FIG. 3B, in one form, a dual system connector 156 aides in increasing the treatment surface area of the wound bed 10. In one form, this optional device may be used to join two or more pieces of the medical tubing 140 (such as through the connectors and leurs 161, 162 the latter of which is shown), which in turn promotes the distribution of the solution to a broader surface area of the wound bed 10. Such an approach is particularly useful for larger, complex conditions (as will be discussed in more detail as follows in conjunction with FIG. 9) with multiple spaced wounds. Although presently shown as a Y-shaped configuration with a single bifurcation into two branches, it will be appreciated that additional branches may be included, depending on the particular wound needs, and that all such variants are deemed to be within the scope of the present disclosure.

Figure 5:
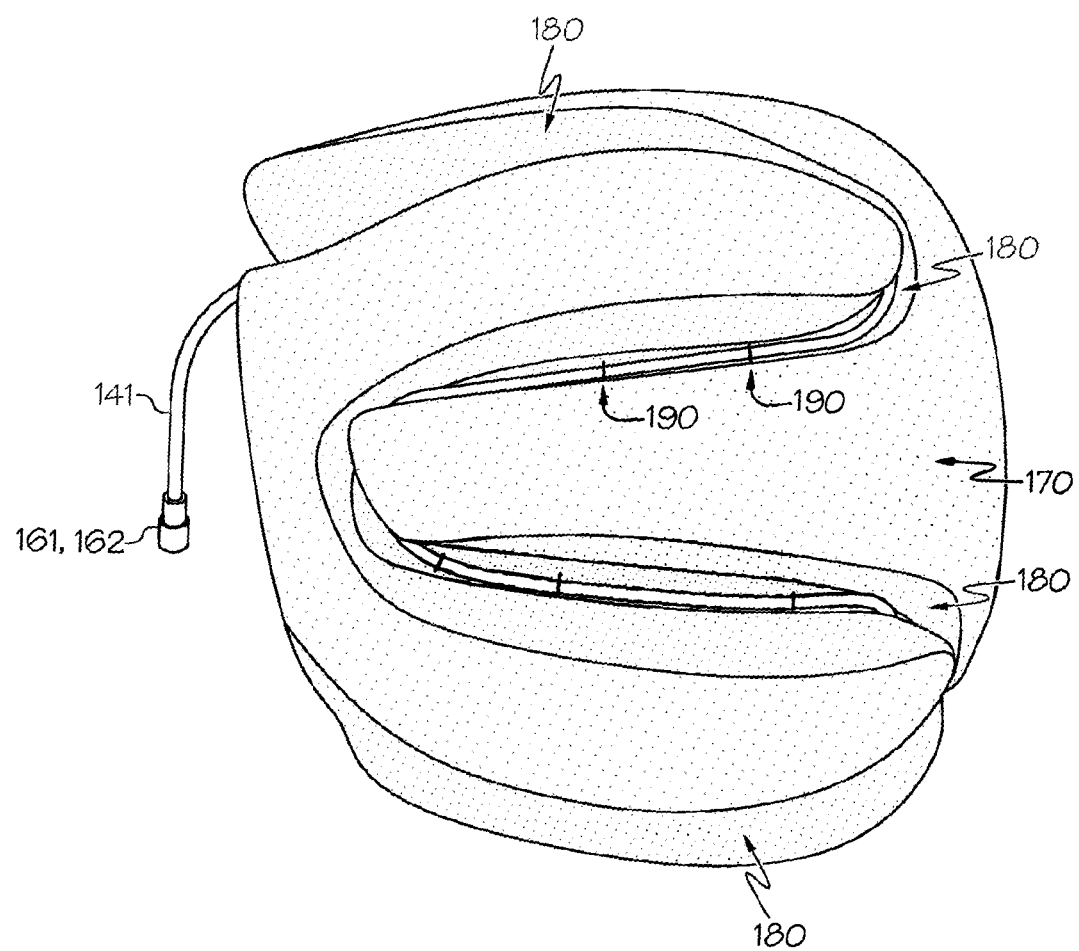
FIG. 5 depicts the use of a section of tubing placed within a preformed sponge in order to form a wound irrigation catheter.

Referring with particularity to FIG. 5, a use of the WIS 100 in the form of the delivery conduit 141 embedded in a notional serpentine-shaped sponge 150 or gauze dressing (not shown) to allow volume distribution control. In this way, when soaking the wound bed 10, improved wound moisture maintenance, irrigation debridement, physical disruption of biofilm and removal of microorganisms may be achieved. When the sponge 150 and delivery conduit 141 of the WIS 100 are used in such a way as depicted in FIG. 5, it may be thought of as a wound irrigation catheter 170 as a way to provide the previously-discussed predetermined delivery path for the irrigation fluid that is being introduced through tubing 140. In one form, the length of time needed to soak the wound bed 10 may be made dependent upon standards, guidelines or related the recommendations of the manufacturer of the irrigation fluid, while in another, based on the goals established by the physician for a particular course of wound therapy, as well as other factors such as wound bed 10 complexity and anatomical location, as well as the patient's ambulatory condition. For example, when using Prontosan® Wound Irrigation Solution, the dwell or soak time recommended by the manufacturer is at least fifteen minutes. In one form, the medical tubing 140 is configured to be part of a larger assembly (including—in some embodiments—as part of the previously-discussed retrofit kit) that may include or otherwise be made to be cooperative with a processor-based controller or related programmable device, sensors and associated circuitry, some of which is discussed in more detail as follows. This in turn could include logic and related circuitry, as well as conduit, valving and related fluid control mechanisms in order to provide feedback capability or related means of irrigation fluid delivery and excess or waste fluid removal. Such an approach may allow for an increased amount of automation of the therapy through controlled irrigation fluid instillation time and dwell time, among others. In a similar manner, the sensors or related detectors may be made signally cooperative with the controller, fluid control mechanisms and the medical tubing 140 to detect leaks, such as those associated with the use of the irrigation fluid delivery source 121 and excess fluid removal source 122. In one form, warnings or alarms such as haptic, audible, visual or related indicia may be used to bring such leak leakage to the physician or other person that is providing care to the wound bed 10. This can be beneficial when checking the integrity of a seal, dressing 130 or other covering to the wound bed 10.

In use, the combination of the delivery conduit 141 and the drainage conduit 142 allows for a customizable porous closed-end system that promotes the generation and maintenance of adequate hydrostatic pressure within medical tubing 140 to ensure a longer emission distance of fluid along tubing length. By being closed-end, it is possible to distribute the irrigation fluid in a more even and efficient manner than if the system were-open-ended. Moreover, because the WIS 100 may be configured as a portable, standalone, compact device, it can be easily assembled and used interchangeably with any gauze or dressing format, including wet-to-dry, NPWT or occlusive.

Referring again to FIG. 2 in conjunction with FIGS. 3A through 4, if the medical tubing 140 is part of a NPWT system, it may, in one form, be fluidly decoupled from one or both of the irrigation fluid delivery source 121 and the excess fluid removal source 122 for times during a procedure where it is desirable to do so. For example, in situations where the irrigation fluid is being infused from the delivery conduit 141 into the wound bed 10 via drip or gravity feed rather than through increased pressure, it may be beneficial to have the pump of the irrigation fluid delivery source 121 or the excess fluid removal source 122 be turned off in order to conserve energy. In such circumstance, one or more clamps may be used to selectively close off the drainage conduit 142. Likewise, in configurations where it is desirable to keep one or both of the fluid delivery source 121 and the excess fluid removal source 122 operational at all times (such as for a prime-reliable type of system), excess flow coming from the delivery conduit 141 or going to the drainage conduit 142 may be diverted or recirculated through suitable valving and additional conduit (not shown), possibly in conjunction with a processor-based controller or related programmable device and one or more signally-coupled flow sensors, pressure sensors or the like as will be discussed in more detail as follows.

In a related way, one or both of the irrigation fluid delivery source 121 and the excess fluid removal source 122 may be configured with the processor-based controller such that programmability features are included. This would allow for variations in irrigation fluid dwell time in the wound bed 10. Such programmability would allow one or both of the irrigation fluid delivery source 121 and the excess fluid removal source 122 to maintain a state of prompt readiness by holding their duty cycles in a standby or related configuration while selectively preventing (for example) the irrigation fluid from infusing during portions of the cycle. In another form, the WIS 100 may be configured to not require any dwell time, such as when the WIS 100 is placed in close proximity to the wound bed 10. Such a reduction (or even elimination) of the dwell time needed for the irrigation fluid to reach the surface of the wound bed 10 is beneficial in that it avoids having the conventional approaches of having the fluid travel through a substantial or even full thickness of a sponge (such as the sponge 150). Significantly, this "close proximity" WIS 100 may be used to minimize instillation volumes required to coat the surface of small and large complex wounds. Moreover, in configurations where the medical tubing 140 of WIS 100 is not part of an NPWT system, it still avoids saturation problems such as those associated with having the dressing 130 and the wound bed 10 becoming too wet, too quickly through the avoidance of conventional NPWT instillation methods that do have such longer dwell times.

Unlike conventional approaches that may instill an irrigation fluid based on certain time periods (that is to say, injection rates or flow rates), the ability of the present medical tubing 140 to inject a certain volume of the fluid (whether by drip or through pressurization) is related instead on the wound size. From there, application of the irrigation fluid may in one form be delivered with a frequency that is determined by physician best practices, while in another based on logic determined by the processor-based controller. In a related way, factors such as the size of or condition of the wound bed 10 may be taken into consideration. For example, for a wound bed 10 that is less than about 20 cm$^2$ in surface area, then about 5 to 10 ccs are delivered three times per day; if the wound bed 10 is between about 20 to 50 cm$^2$, then about 10-20 ccs are delivered three times per day; if the wound bed 10 is between about 50 to 100 cm$^2$, then about 20-30 ccs are delivered three times per day; if the wound bed 10 is between about 100 and 200 cm$^2$, then about 30-40 ccs are delivered three times per day; if the wound bed 10 is greater than about 200 cm$^2$ in surface area, then about 50 ccs three times per day. Likewise, a clean wound bed 10 may require three times per day, as does a wound bed 10 that is between being clean to contaminated, whereas a contaminated wound bed 10 may require delivery of fluid four times per day, and where there is heavy colonization or in a desiccated state, perhaps every two to four hours.

Referring again to FIG. 5, the medical tubing 140 in general and one or both of the delivery conduit 141 and drainage conduit 142 may be arranged in a particular pattern as needed by the bed of the wound bed 10 such that the wound irrigation catheter 170 is formed. In one form, one or more of the size or shape of the apertures 145 may be made to vary along the length of the tubing 140 in order to further promote or customize the hydrostatic pressure. In the particular form shown, a serpentine-like canal (or channel) 180 construction within the sponge 150 shows how such sponges 150, gauze dressings that make up the wound irrigation catheter 170 are created specific to the size dimensions of wound bed 10. These canals 180 channel the steady flow of irrigation fluid or related solutions over specified areas of the wound bed 10, and may be constructed at varied depths in a circular, oval, vertical, horizontal or grid-like fashion to house the medical tubing 140 in close proximity to wound bed 10. The construction of the canals 180 may be performed in a layered, vertical or horizontal fashion within the sponge 150, thereby allowing a customizable layered instillation delivery, regardless of the thickness of the wound bed 10. For example, in a relatively shallow wound, a single layer of the sponge 150 and channel 180 may be formed, whereas for a thicker wound, multiple layers of the sponge 150 and channel 180 may be formed each to allow the insertion of the delivery conduit 141 of WIS 100. This promotes delivery of solutions low in the dressings in close proximity to the wound bed 10, as well as in various other places throughout the thickness of the wound bed 10. This in turn helps to avoid excessive amounts of volume instillation into the sponge 150 prior to saturating the bed of the wound bed 10 that may otherwise be needed.

In one form, the canals 180 may be created simply by carving a grid-like pattern into the foam of the sponge 150 using a scalpel blade, where it will be appreciated that the size of and pattern of the canals 180 may vary depending upon the size and condition of the wound. In another form, the sponge 150 may include in situ-formed canals 180 at the time of sponge 150 manufacture. In this latter form, what such a pre-formed sponge 150 and the related wound irrigation catheter 170 may give up in customizable canal 180 patterns is compensated for by gains in faster, low-cost operation at the end-use location. Stainless steel staples 190 (also referred to as surgical clips) may be used to anchor the medical tubing 140 at various locations within the sponge 150. The use of such staples 190 may be particularly beneficial in catheter-based configurations where torturous bending paths of a higher stiffness tubing material are used and may need additional structural reinforcement in order to keep the intended shape.

Regardless of whether the WIS 100 is being used as part of an NPWT or gauze-based approach, irrigation fluids may be one or more of Dakins, Sulfamylon® (or a related mafenide acetate), acetic acid, silver nitrate, Vashe® and normal saline. As previously discussed, the apertures 145 of the delivery conduit 141 permit dripping, spraying or seepage of such solutions into NPWT sponges 150 (whether or not formed as part of a wound irrigation catheter 170) or gauze dressings in an efficient, controlled manner (including volume distribution control) along a designated portion of a wound bed 10. Also as previously mentioned, such an approach aides in wound moisture maintenance, irrigation debridement and physical disruption of biofilm, as well as of the removal of microorganisms. With regard to gauze-based wound therapy, it will be appreciated that both single layer and multilayer approaches may be used, and that both single layer and multilayer variants are within the scope of the present disclosure. For example, a layer of gauze 107 may be placed within the wound bed 10 after which the delivery conduit 141 is placed on top, to be followed by a top layer of the gauze 107 such that both may receive moistening in a uniform manner. It will be appreciated that the configuration of the packing 105 or gauze 107 may be in sheet or packing form, depending on the need of the wound bed 10. It will also be appreciated that the packing 105 or gauze 107 may be the same material, also configured for a particular use. For example, in one form, the packing 105 may be formed from the gauze 107 by folding over on itself one or more times, whereas in another form, its as-manufactured form resembles a thicker three-dimensional volumetric structure. Likewise, these and other such forms of the packing 105 or gauze 107 are deemed to be within the scope of the present disclosure.

Although not shown, an augmented wet-to-dry embodiment of the WIS 100 according to an aspect of the present disclosure is also within the scope of the present disclosure. In such an embodiment, the medical tubing 140 in the form of the delivery conduit 141 is placed in fluid communication with a piece of packing, gauze, sponge or related material that has been placed within the cavity of the wound bed 10. In this way, the packing may be rewetted on an as-needed basis without having to disturb the cover or related wound-protective layer. Thus, and in addition to being usable to manage fluids being delivered to and removed from a wound bed 10 in conjunction with an NPWT-based dressing, the WIS 100 can be universally applied to any occlusive, gauze or related dressing (any one of which may be representative of dressing 130), thereby promoting ease of outpatient use, as well and decrease in the frequency of dressing 130 changes. As such, particularly when embodied as a kit, assembly or related structure, the ease of use of medical tubing 140 need not be only for inpatient or skilled healthcare facility, home health aide or the like where a skilled healthcare provider is available, but also for family members and—depending on the severity of the wound—to the individual patient. As will be discussed in conjunction with FIG. 10, in one form where the medical tubing 140 forms part of a larger system that may include a processor-based controller, the cooperation of the sensors, circuitry and processor—in conjunction with suitable logic and wired or wireless radio technology that forms part of the controller—can be made to automatically send message-based updates to the patient, family member, health care provider or other interested party to alert the receiver of the message that a dressing 130 change may be necessary. In such form, the system 100 may engage in data exchange with a third party through standardized protocols such as those associated with public-private key exchanges, hypertext transfer protocol (HTTP), secure HTTP (HTTPS), advanced encryption standard (AES), web service or native application programming interfaces (APIs, that is to say, "apps"), including those that are resident on a mobile telephone or related telecommunication device or other electronic information exchange approaches. Similarly, in one form, the exchange of data between the system 100 and the third party may take place over the internet, VPN, local area network (LAN), wide area network (WAN) or related packet-switched network.

Figure 6B:
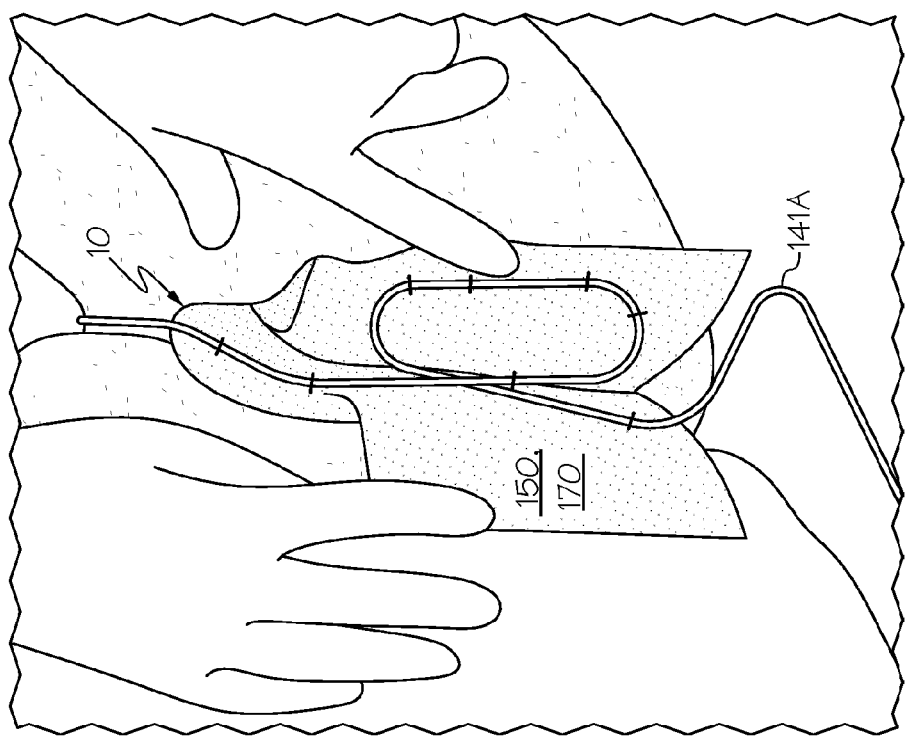
FIGS. 6A and 6B depict canal construction and WIS placement of a wound irrigation catheter for a wound with a flat surface and for a wound that is lengthy and deep vertically with several areas of recess and tunneling, respectively.
Figure 6A:
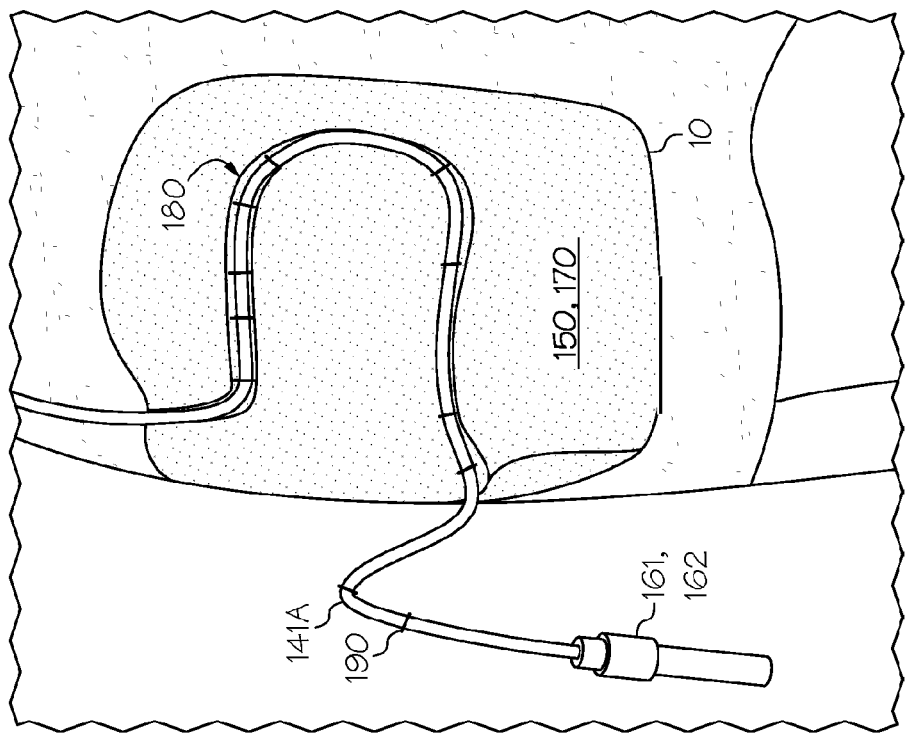

Referring next to FIGS. 6A and 6B, details associated with a method of canal construction and WIS 100 placement for two different wound types are shown. Referring with particularity to FIG. 6A, a wound bed 10 that is defined by a relatively flat surface may receive a simple, single-piece embodiment of the sponge 150 and relatively simple WIS 100 pattern, whereas for a wound bed 10 that is lengthy and deep vertically with several areas of recess and tunneling as shown with particularity in FIG. 6B, the wound may be filled with a compound embodiment of the sponge 150 (including one or more of the single-layer or multilayer embodiments previously discussed) with WIS 100 having one or more layers, overlaps, switchbacks or related placement patterns.

Figure 7A:
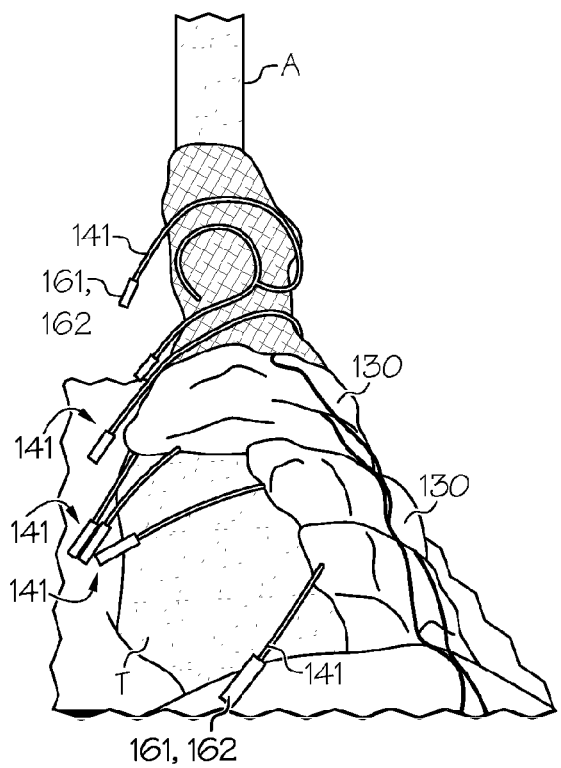
FIGS. 7A through 7C depict an arm wound being treated post-operatively with an embodiment of the WIS according to an aspect of the present disclosure.
Figure 7C:
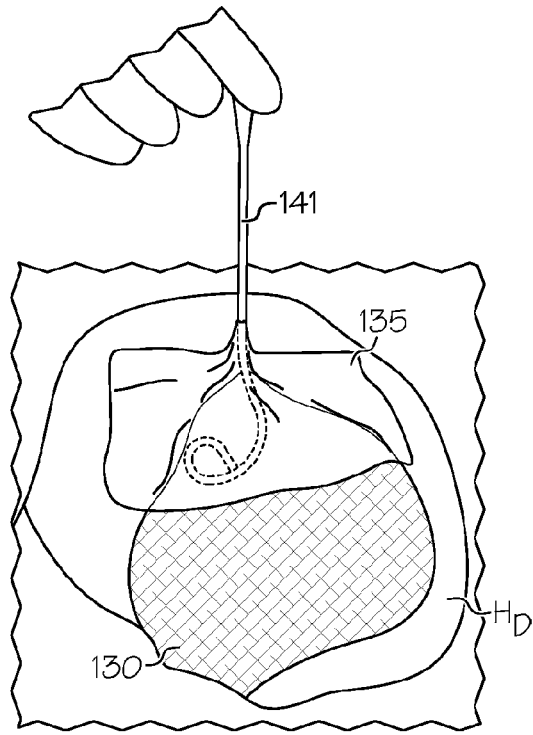
Figure 7B:
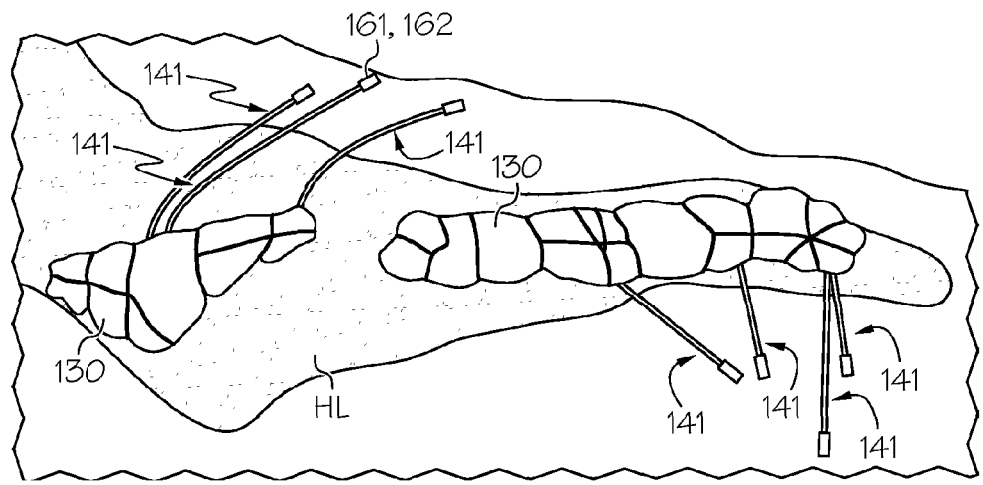

Referring next to FIGS. 7A through 7C, details associated with a post-operative wound irrigation using an embodiment of the WIS 100 are shown. For example, FIG. 7A shows a split thickness skin graft for a left upper arm A and left lateral torso T with a bolster dressing 130 status post-split-thickness skin grafting with multiple WIS 100 placements intertwined within the bolster dressing 130. Similarly, FIG. 7B shows a hip and leg HL with multiple WIS 100 placements intertwined within the bolster dressing 130. As can be seen in both of these configurations, the anti-microbial irrigation fluid is introduced over the skin grafts via the numerous fluid delivery conduits 141. In a different manner, FIG. 7C shows a chronic hip HD decubitus ulcer wound with an occlusive wet-to-dry dressing 130 where the single fluid delivery conduit 141 of WIS 100 is placed beneath. In one form, the occlusive dressing 130 of FIG. 7C may be similar to the bolster dressing 130 of FIGS. 7A and 7B, and additionally may include an optional non-porous coating 135 (such as through the use of wax or the like) in order to selectively reduce or eliminate the absorbent properties that are typically associated with gauze or other porous media.

Figure 8A:
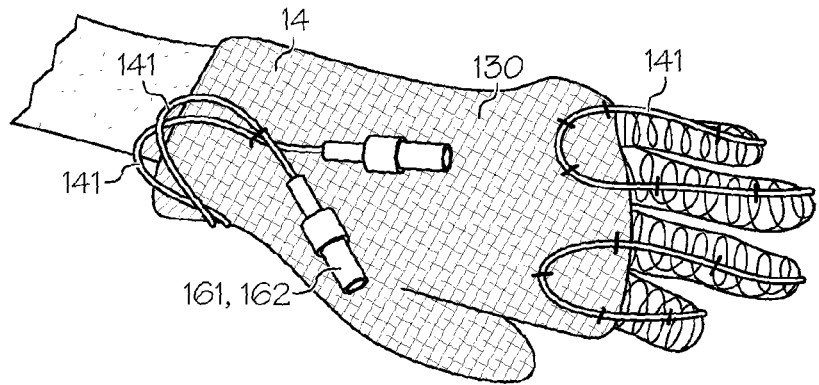
FIGS. 8A through 8C depict a hand wound being treated post-operatively with an embodiment of the WIS according to an aspect of the present disclosure.
Figure 8B:
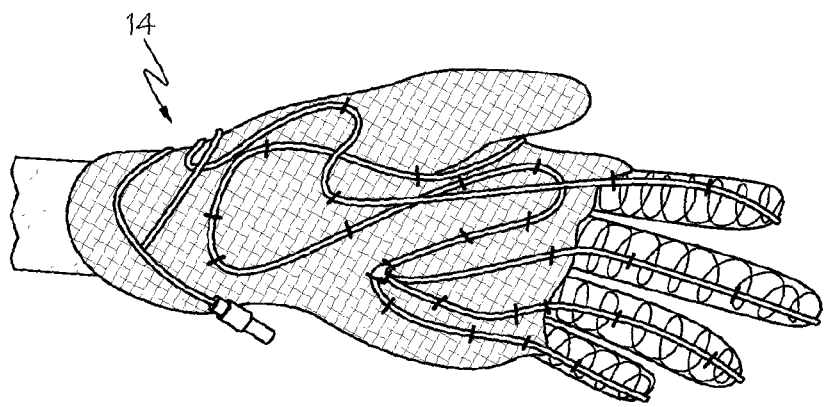
Figure 8C:
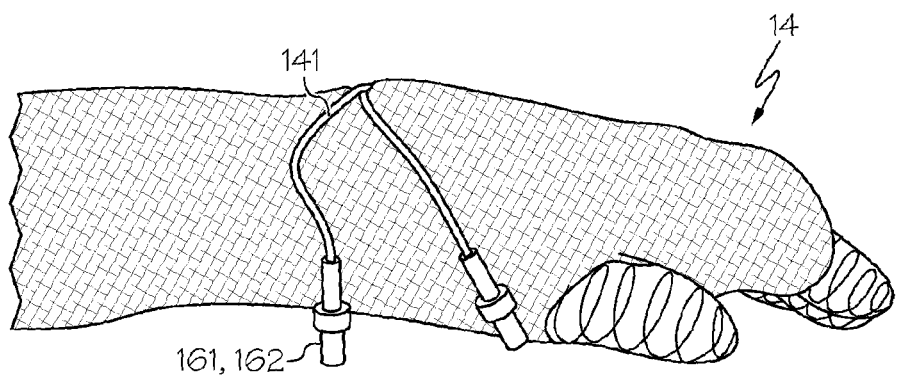

Referring next to FIGS. 8A through 8C, details associated with a post-operative wound irrigation for a skin graft for a hand H are shown using an embodiment of the WIS 100. Referring with particularity to FIGS. 8A and 8B, an application to a split thickness skin graft can be seen, where the WIS 100 is placed directly over the areas of skin graft, including the ventral and dorsal surface of the fingers. Referring with particularity to FIG. 8C, a final dressing with WIS 100 is shown, where more than one (presently shown as two) particular or different irrigation solutions or fluids may be delivered, each through a dedicated fluid delivery conduit 141.

Figure 9:
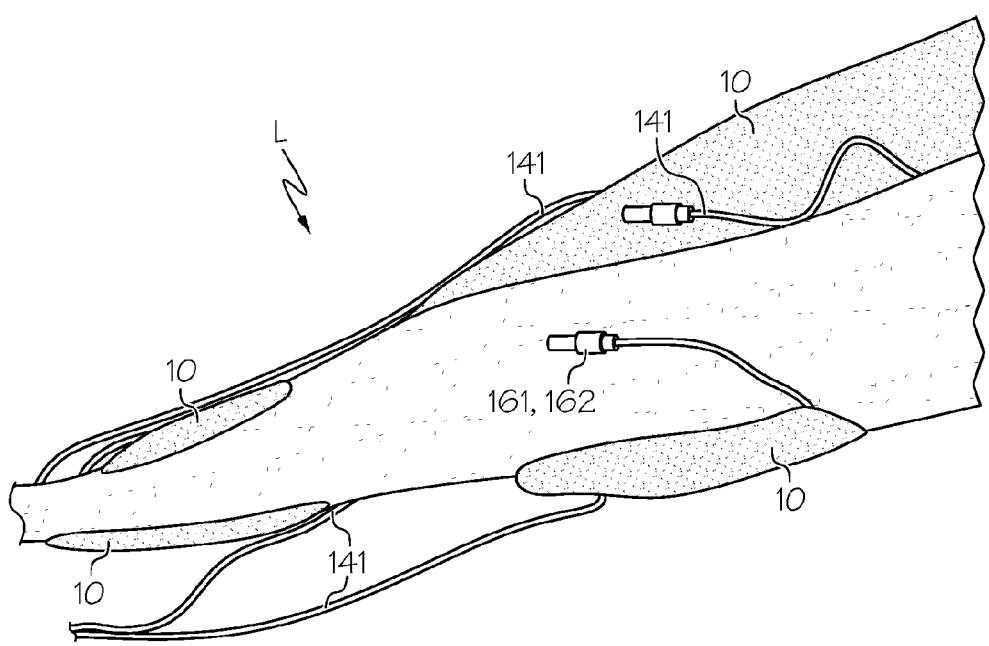
FIG. 9 depicts the use of a WIS used to help treat a large wound in the form of a series of disparate wounds that are located at different areas along the upper and lower leg.

Referring next to FIG. 9, details associated with using an embodiment of the WIS 100 in a leg L with multiple spaced wounds are shown. In particular, two WIS 100 placements that cover four separate large leg wounds across both the upper and lower portions of the leg L can be seen, where one WIS 100 is placed in the medial left upper and lower leg NPWT dressing, and one WIS 100 to the lateral left upper and lower leg NPWT dressing. In situations such as this (as well as those of FIGS. 7A and 7B that show numerous catheters placed in different wound locations), the use of the WIS 100 in conjunction with one or both of a moisture monitoring device 200 and wound irrigation treatment system 300 (both of which are discussed in more detail in conjunction with FIG. 10) may be beneficial, as wound irrigation needs may differ from location to location, even within a common body part.

Although not shown, numerous other medical procedures may be performed using the WIS 100 along with an NPWT-based wound treatment, including those for large, complex necrotizing soft tissue infection (NSTI) wounds, Fournier Gangrene Cases or the like. In one exemplary form, an irrigation system based on WIS 100 can be placed beneath large preserved flaps of skin during skin and soft tissue-sparing surgery of various NSTI wounds.

Figure 10:
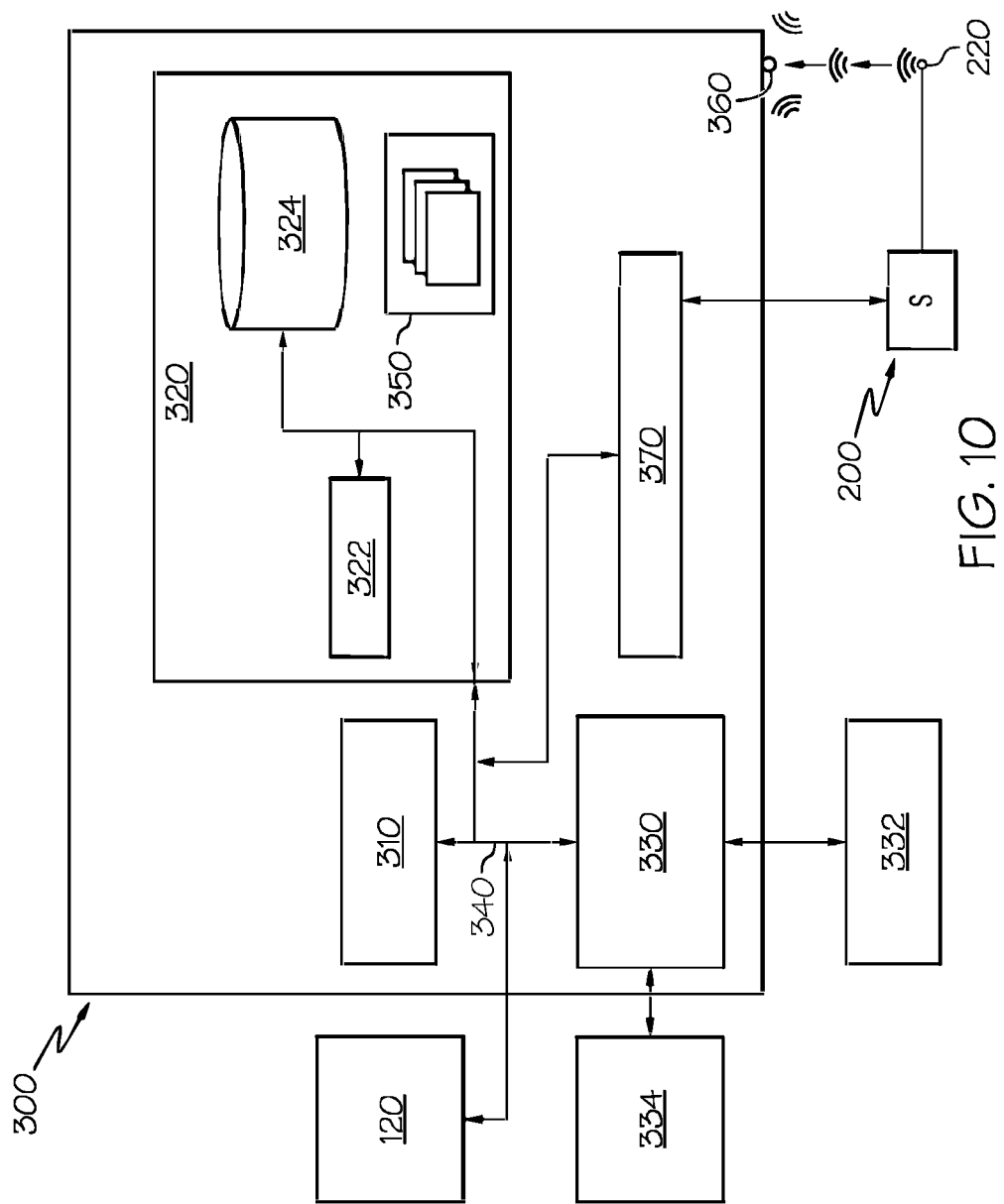
FIG. 10 depicts schematically the WIS being used as part of an optional wound irrigation monitoring system and optional wound irrigation treatment system.

Referring next to FIG. 10, regardless of whether the medical tubing 140 is being used as part of an NPWT-based embodiment or an augmented wet-to-dry embodiment of the WIS 100, it may in one form be part of a larger assembly that may include a moisture monitoring device 200 that forms a part of—or is otherwise signally cooperative with—the NPWT device 120 and other parts of the wound irrigation treatment system 300. As such, the WIS 100 may be made to cooperate with—or be an integral part of—one or both of the moisture monitoring device 200 and the NPWT device 120, while both of the moisture monitoring device 200 and NPWT device 120 may in turn be configured as part of a larger assembly within the wound irrigation treatment system 300, and that all such structural, functional and interconnectivity variants are deemed to be within the scope of the present disclosure.

The moisture monitoring device 200—which may include one or more sensors S for the acquisition of moisture, pressure, flow, temperature or one or more other forms of sensory data—may be signally coupled via wired 210 or wireless 220 connection to the wound irrigation treatment system 300 that in one form may be equipped with a suitable algorithm that in one form may be combined to perform various fluid monitoring and optional fluid recirculation, diversion or related management functions. In one form, the moisture monitoring device 200 and NPWT device 120 may be made to cooperate with the WIS 100 and packing 105, gauze 107, sponge 150 (also referred to as an NPWT sponger) or the like such that upon detection of sensory data that exceeds a certain threshold value, one or more of an alert or correction action may be taken. One example of a threshold that may be exceeded is that pertaining to a moisture level within the wound bed 10. On particular, if the wound bed 10 is in danger of either drying out or becoming overly wet such that a sensed value is outside an acceptable range of moisture levels, an alert may be generated and sent to an appropriate caregiver, as well as to actively instruct a source of the irrigation fluid to change the amount of fluid being delivered to the wound bed 10 in a controlled manner. In this way, appropriate corrective action may be taken (either by caregiver intervention or automatically). In a like manner, other data, such as temperature, pressure or excessive movement may be monitored by correspondingly-configured sensors S. For example, if movement of a patient who is receiving wound irrigation therapy is to be avoided, one or more sensors S that are configured to sense movement through an accelerometer, gyroscope, magnetometer, altimeter, motion detector, inertial measurement unit (IMU) or the like may be used.

As previously discussed in conjunction with FIG. 2, the NPWT-based embodiment of the WIS 100 that includes the NPWT device 120 may be made to cooperate with an optional dressing or related wound seal 130. In one form as shown, the NPWT-based embodiment also includes (or can otherwise be configured to cooperate with) one or both of the moisture monitoring device 200 and the controller that makes up a portion of the wound irrigation treatment system 300. In this last form, the wound irrigation treatment system 300 may be configured as a controller that in one form is configured as a general-purpose computing device that may include—among other things—one or more processors or processing units 310, computer-readable media in the form of memory 320, and input/output (I/O) 330, all signally coupled via bus 340. The processor (also referred to as a central processing unit (CPU) or the like) 310 may include modules to perform various arithmetic, control logic and related processing functions. In one form, the memory 320 in readable or writable form may include both volatile media 322 (such as random access memory, RAM, cache or the like, in one form for the storage of data) and non-volatile media 324 (such as read-only memory, ROM, often in the form of flash, hard disks, optical disks such as compact disks (CDs), digital video disks (DVDs) or the like, in one form for the storage of programs for various algorithmic control logic-based operations), as well in removable and non-removable media configurations. Memory 320 may be connected to the bus 340 by one or more data media interfaces. In one form, I/O 330 input 332 is configured as a keyboard, mouse, verbal command, joystick or other known means, while output 334 may be in the form of video display, audio message or other known means. Although the bus 340 is shown as a wired connection, it will be appreciated that it may be configured to have at least some of its functionality embodied in a wireless format (including the transmitting or receiving of radio-frequency signals via antenna 360, and that all such variants are deemed to be within the scope of the present disclosure. In addition, the use of terms "controller 300" and "wound irrigation treatment system 300" are used interchangeably within the present disclosure; circumstances where greater precision is intended will be apparent from the context.

One or more programs 350 to carry out one or more operations or methodologies as discussed herein (including those corresponding to moisture monitoring by sensors S and irrigation fluid delivery) may be stored in memory 320. By way of example, and not limitation, such programs 350 may include an operating system, one or more application programs, program data or the like, as well as programs for network connectivity such as through a suitable communication protocol including one or more of the previously-discussed LAN or WAN, as well as a public network (such as the internet), a WiFi network or the like, along with a suitable network adapter 370 or other bus-enabled interface. In one form, such connectivity may be through a distributed, remote environment such as a cloud (not shown). In such a distributed configuration, various modules making up one or more parts of the program or programs 350 may be located in both local and remote computer system storage media, including those discussed herein. In one form, the program or programs 350 may be in modular format such that each module generally carries out one or more discrete functions or tasks of the functions and/or methodologies of embodiments of the WIS 100 as described herein. These modules may include—among other things—various instruction sets, logic, programs, routines, objects, components, data structures or the like in order to perform particular tasks or implement particular abstract data types.

In one form, data that is generated by the moisture monitoring device 200, the NPWT device 120 or other parts of the wound irrigation treatment system 300 may be made available for use physicians, nurses or other interested people through a computer, mobile telephone or other client device so that such interested person or persons may query the moisture status of the wound. In one form, the data may be in raw (that is to say, unprocessed) format, while in another, after having been subjected to one or more pre-programmed (that is to say, deterministic) or machine-learning approaches. By way of example, such data may be exchanged via web-based portal, a cloud-based computing system, a back-end server or the like. Such exchange may take place either locally (such as through intranet or related private network connectivity) or remotely, such as through internet connectivity.

In one form, the wound irrigation treatment system 300 is generally referred to as having a von Neumann architecture, and as such is configured to perform specific automated steps consistent with the various procedures, methods, steps and related operations that are used in conjunction with the WIS 100 and moisture monitoring device 200 as outlined in this disclosure. Upon having portions or all of the programs 350 loaded into memory 320 in general (and in one form into ROM or other non-volatile media 324 in particular), the wound irrigation treatment system 300 becomes a specific-purpose machine configured to determine the parameters associated with the operation of the WIS 100 and moisture monitoring device 200 in a manner as described herein. In one form of operation, source code (such as that created by a programmer) may be converted into executable form as machine code for use by the processor 310; such machine code is predefined to perform a specific task in that it is taken from a machine language instruction set known as the native instruction set that may be part of a shared library or related non-volatile portion of memory 320 and that is specific to the implementation of the processor 310 and its particular Instruction Set Architecture (ISA). This in turn allows the processor 310 to perform a predefined set of operations in response to receiving a corresponding instruction selected from the predefined native instruction set, where at least a portion of the program or programs 350 include a set of machine codes selected from the native instruction set and operated upon by the processor 310 and other portions of the wound irrigation treatment system 300 to perform one or more of the moisture monitoring and wound irrigation operations as described herein. One such use of the moisture monitoring device 200 or wound irrigation treatment system 300 is as part of a records maintenance system where data, analytics or related medical-relevant information gleaned from the device or system may be sent to a particular patient's electronic medical record (EMR) or the like for either periodic or as-needed updating.

Furthermore, algorithms that make up one or more of the programs 350 may either form a part of or be made cooperative with a machine learning model such that at least some of the data being acquired by the sensor or sensors S may be analyzed by the model to allow the model to learn for itself and make suitable predictions. In one form, such predictions may include those that can include correlations between the sensed data and whether a need exists to change one or both of the moisture and humidification level within the cavity of the wound bed 10. Moreover, when used in conjunction with the machine learning model, the wound irrigation treatment system 300 may be configured as an analytics engine. As with the previously-discussed data, predictive analytics such as that available from a machine learning model may be made available for use physicians, nurses or other interested people in order to determine the moisture status of the wound, as well as whether a particular treatment or protocol needs to be adjusted.

Regardless of whether the WIS 100 is operated manually or in conjunction with one or both of the moisture monitoring device 200, the NPWT device 120 or other parts of the wound irrigation treatment system 300, its closed-ended construction coupled with the axially-spaced apertures 145 enhances its ability to deliver irrigation fluid in a designated amount and frequency in a consistent, distributed manner to enhance moist wound healing while at the same time providing cost effective and efficient cleansing, debridement and biofilm reduction in such wounds. In particular, using the WIS 100 in conjunction with existing gauze dressings and negative pressure systems promotes the efficient utilization of anti-microbial solutions that in turn enhances a cost-effective reduction in microorganisms and decolonization. Moreover, the WIS 100 allows for a moist wound healing cascade in the home environment that is not available through traditional instillation negative pressure systems. Although presently shown as being a separate component from—yet still signally cooperative with—the wound irrigation treatment system 300, it will be appreciated that in another form, one or both of the NPWT device 120 and the moisture monitoring device 200 may be formed as an integral part of the wound irrigation treatment system 300, and that all variants, as well as combinations thereof, are within the scope of the present disclosure.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Within the present disclosure, the use of the prepositional phrase "at least one of" is deemed to be an open-ended expression that has both conjunctive and disjunctive attributes. For example, a claim that states "at least one of A, B and C" (where A, B and C are definite or indefinite articles that are the referents of the prepositional phrase) means A alone, B alone, C alone, A and B together, A and C together, B and C together, or A, B and C together. By way of example within the present context, if a claim recites that the wound irrigation treatment system may selectively adjust at least one of an amount of irrigation fluid and an amount of excess fluid, and if such adjustment is the addition or removal of one or both of the irrigation and excess fluids, then such data acquisition satisfies the claim.

Within the present disclosure, the following claims are not written in means-plus-function format and are not intended to be interpreted based on 35 USC 112(f) unless and until such claim limitations expressly use the phrase "means for" followed by a statement of function void of further structure.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A wound irrigation system comprising:
a delivery conduit with a proximal end and a closed distal end fluidly separated by a medial portion to define an irrigation fluid flowpath thereby, the medial portion defining a plurality of apertures extending along a length and through a wall thereof such that at least a majority of an irrigation fluid that is introduced within the delivery conduit at its proximal end is placed in fluid communication with a wound bed through the medial portion; and
at least one intraluminal valve placed in fluid communication with the delivery conduit to maintain hydrostatic pressures of the irrigation fluid, and wherein the at least one intraluminal valve comprises an upstream valve, an interstitial chamber, and a downstream valve;
the upstream and downstream valves are mechanically configured to be closed at rest;
the upstream and downstream valves are mechanically configured to open in response to a predetermined pressure threshold; and
the opening of the upstream and downstream valves defines an orifice through which the irrigation fluid may pass through the upstream valve, the interstitial chamber, and the downstream valve, to a downstream location within the delivery conduit.

2. The wound irrigation system of claim 1, further comprising at least one fitting configured to be secured to the delivery conduit.

3. The wound irrigation system of claim 2, wherein the closed distal end is created by at least one of an end cap and a clip.

4. The wound irrigation system of claim 3, wherein the at least one fitting comprises a female connector and a male fitting fluidly secured to the delivery conduit proximal end.

5. The wound irrigation system of claim 1, further comprising a drainage conduit for removal of fluid from the wound bed, the drainage conduit comprising a proximal end, a distal end and a medial portion to define a fluid removal flowpath thereby.

6. The wound irrigation system of claim 5, wherein the drainage conduit is substantially devoid of any apertures formed through the wall thereof.

7. The wound irrigation system of claim 5, wherein the delivery conduit is structurally decoupled from the drainage conduit.

8. The wound irrigation system of claim 1, further comprising a sponge that defines a channel therein such that upon assembly of the delivery conduit and the sponge, at least some of the medial portion is situated within the channel.

9. The wound irrigation system of claim 1, further comprising a wet-to-dry dressing that is configured to have at least a portion of the delivery conduit attached thereto.

10. The wound irrigation system of claim 1, wherein the upstream flap-like valve is configured to open in response to a different predetermined pressure threshold than the downstream flap-like valve.

11. A wound irrigation treatment system comprising:
a negative pressure wound therapy device comprising an irrigation fluid delivery source and an excess moisture removal source;
a delivery conduit with a proximal end and a closed distal end fluidly separated by a medial portion to define an irrigation fluid flowpath thereby, the medial portion defining a plurality of apertures extending along a length and through a wall thereof such that at least a majority of an irrigation fluid that is introduced from the negative pressure wound therapy device to the proximal end of the delivery conduit is placed in fluid communication with a wound bed through the medial portion;
at least one intraluminal valve placed in fluid communication with the delivery conduit to maintain hydrostatic pressures of the irrigation fluid; and
a drainage conduit placed in fluid communication with the excess moisture removal source, the drainage conduit defining a proximal end, a distal end and a medial portion to define a fluid removal flowpath thereby, and wherein
the at least one intraluminal valve comprises an upstream valve, an interstitial chamber, and a downstream valve;
the upstream and downstream valves are mechanically configured to be closed at rest;
upstream and downstream valves are mechanically configured to open in response to a predetermined pressure threshold; and
the opening of the upstream and downstream valves defines an orifice through which the irrigation fluid may pass through the upstream valve, the interstitial chamber, and the downstream valve, to a downstream location within the delivery conduit.

12. The wound irrigation treatment system of claim 11, further comprising:
a moisture monitoring device configured to acquire at least one form of sensory data from the wound bed; and
a controller that is signally-coupled to the moisture monitoring device and cooperative with the negative pressure wound therapy device such that upon receipt by the controller of a signal that exceeds a wound irrigation threshold, the wound irrigation treatment system may selectively adjust at least one of (a) an amount of irrigation fluid that is being delivered to the wound bed through the delivery conduit and (b) an amount of excess fluid present within the wound bed.

13. A method of using a wound irrigation system, the method comprising:
configuring tubing to comprise:
a delivery conduit that defines a proximal end and a closed distal end fluidly separated by a medial portion to define an irrigation fluid flowpath thereby, the medial portion defining a plurality of apertures extending along a length and through a wall thereof, and
at least one intraluminal valve placed in fluid communication with the delivery conduit to maintain hydrostatic pressures of an irrigation fluid, wherein:
the at least one intraluminal valve comprising an upstream valve, an interstitial chamber, and a downstream valve,
the upstream and downstream valves are mechanically configured to be closed at rest,
the upstream and downstream valves are mechanically configured to open in response to a predetermined pressure threshold, and
the opening of the upstream valve and downstream valves defines an orifice through which the irrigation fluid may pass through the upstream valve, the interstitial chamber, and the downstream valve, to a downstream location within the delivery conduit; and
arranging the tubing such that upon placement of the tubing in fluid communication with a wound bed by a user, the introduction of the irrigation fluid into the proximal end of the delivery conduit causes at least a majority of the irrigation fluid to flow to the wound bed through the medial portion.

14. The method of claim 13, wherein the irrigation fluid is delivered by drip irrigation.

15. The method of claim 13, further comprising configuring the delivery conduit to be placeable in fluid communication with a negative pressure wound therapy device that comprises an irrigation fluid delivery source such that upon fluid connection thereto and operation thereof, the negative pressure wound therapy device and the delivery conduit cooperate to introduce irrigation fluid to the wound bed.

16. The method of claim 15, further comprising configuring the tubing to comprise a drainage conduit to be placeable in fluid communication with the negative pressure wound therapy device such that upon fluid connection thereto and operation thereof, the negative pressure wound therapy device and the drainage conduit cooperate to remove excess fluid from the wound bed.

17. The method of claim 13, further comprising configuring the tubing to be placeable in fluid communication with a wet-to-dry dressing.

18. The method of claim 13, further comprising configuring a moisture monitoring device such that upon placement thereof in relation to the wound bed that at least one form of sensory data is acquired therefrom, a signally-coupled wound irrigation treatment system may selectively adjust an amount of irrigation fluid being delivered to the wound bed through the delivery conduit.

* * * * *